United States Patent [19]

Park et al.

[11] Patent Number: 5,694,118
[45] Date of Patent: Dec. 2, 1997

[54] GAS DETECTION AND ALARM SYSTEM FOR MONITORING GAS SUCH AS CARBON MONOXIDE

[76] Inventors: Sea C. Park; In P. Park, both of 3836 Birchwood, Skokie, Ill. 60076

[21] Appl. No.: 365,290

[22] Filed: Dec. 28, 1994

[51] Int. Cl.⁶ ............................................. G28B 17/10
[52] U.S. Cl. .......................... 340/632; 340/633; 340/634; 340/628; 73/23.21
[58] Field of Search ........................... 340/632, 633, 340/634; 73/23.21, 23.31, 31.01, 31.02, 31.03; 346/628; D13/139

[56] References Cited

U.S. PATENT DOCUMENTS

| | | | |
|---|---|---|---|
| 1,313,089 | 8/1919 | Ile | D13/139 |
| 3,246,312 | 4/1966 | McGinn | 340/632 |
| 3,445,669 | 5/1969 | Jordan et al. | 340/632 |
| 4,498,330 | 2/1985 | Hosoya | 73/23.21 |
| 4,688,021 | 8/1987 | Buck et al. | 340/632 |
| 4,839,014 | 6/1989 | Park et al. | 340/632 |
| 4,893,113 | 1/1990 | Park et al. | 340/632 |
| 5,132,659 | 7/1992 | Kuo | 340/326 |
| 5,239,980 | 8/1993 | Hilt et al. | 126/116 A |

FOREIGN PATENT DOCUMENTS 2276970  10/1994  United Kingdom ............... 340/632

8606528  11/1986  WIPO ............................... 340/632

OTHER PUBLICATIONS

Figaro Gas Sensor TGS203 (Gas Detection Device for Carbon Monoxide); Figaro Engineering Inc., Osaka Japan; pp. 1-16; Aug. 1990.

*Primary Examiner*—Brent A. Swarthout
*Assistant Examiner*—Van T. Trieu

[57] ABSTRACT

A gas detection and alarm system and a method thereof for monitoring a predetermined dose of carbon monoxide and other gases in the atmosphere which can be harmful to humans, having a gas detection/alarm device comprising a detection circuit which detects a predetermined dose of a gas such as carbon monoxide, an indication circuit which visually and audibly indicates the dose detection to the user based on the detection circuit, a microprocessor for digitally operating the detection circuit and the indication circuit, a power conversion circuit which converts AC power to DC power without using any transformers and which supplies the converted constant power to the detection circuit, indication circuit and microprocessor, and a housing which compactly houses the detection circuit, indication circuit, power conversion circuit and microprocessor.

8 Claims, 8 Drawing Sheets

GAS DETECTION AND ALARM SYSTEM FOR MONITORING GAS SUCH AS CARBON MONOXIDE

CROSS REFERENCE TO RELATED APPLICATIONS

This application is related to application Ser. No. 133,924 entitled "CLEANER ASSEMBLY, HUMIDIFIER, GAS ALARM, AND DETOXIFICATION SYSTEM" filed Nov. 16, 1987, now U.S. Pat. No. 4,839,014, which is hereby incorporated by reference.

BACKGROUND OF THE INVENTION

1. Field of the Invention

The present invention relates to a gas detection and alarm system for monitoring gas such as carbon monoxide. More particularly, the present invention relates to a gas detection and alarm system having a digital gas detection/alarm circuit for audibly and visually indicating a detection of a predetermined level of a gas such as carbon monoxide. Furthermore, the present invention relates to a gas detection alarm system having a variable strobe light indicator for visually indicating the gas detection to the user.

2. Description of the Background Art

FIG. 1 shows a block diagram of a conventional gas detection and alarm system. The conventional system comprises a current supply 200, a constant DC circuit 202 for supplying constant DC power to a sensing unit 206 which senses a dose of gas, such as carbon monoxide, present in the atmosphere, a power failure back-up circuit 204 for supplying alternative power in the event of a power failure, and a detection circuit 210 which determines whether or not a predetermined dose of gas, such as carbon monoxide, which is harmful to humans, exists. A sensitivity controller 208 having a variable resistor is used to control the sensitivity of the sensing unit 206 by varying the resistance of the resistor. When the predetermined gas level is detected by the detection circuit 210, an alarm circuit 212 is activated to generate alarm signal 214. The alarm signal 214 audibly alerts the user that a harmful level of gas, such as carbon monoxide, exists in the atmosphere.

The conventional gas detection and alarm system utilizes a plurality of transformers and analog electronic circuits, which results in a large-sized, heavy and expensive gas detection and alarm system for monitoring gas such as carbon monoxide. Furthermore, it is difficult for the hearing-impaired user to employ the conventional system because the conventional system lacks visual indicators which strongly indicate the predetermined dose detection to the user.

SUMMARY OF THE INVENTION

Accordingly, it is an object of the present invention to provide a gas detection and alarm system having a digital detection/alarm circuit for audibly and visually indicating a predetermined gas level detection to the user.

Another object of the present invention is to provide a gas detection and alarm system for monitoring gas such as carbon monoxide, having a transformerless AC to DC power conversion circuit for supplying constant DC power to the gas detection/alarm circuit, thereby providing a light-weight, inexpensive, small-sized gas detection and alarm system.

Another object of the present invention is to provide a gas detection and alarm system for monitoring gas such as carbon monoxide, having a variable strobe light indicator for visually alerting the user of a predetermined gas dose detection.

Another object of the present invention is to provide a gas detection and alarm system for monitoring gas such as carbon monoxide, having a gas detection/alarm device which is capable of engaging with a light bulb socket or an electric outlet.

Still another object of the present invention is to provide a gas detection and alarm system for monitoring gas such as carbon monoxide, wherein the system is incorporated into a socket adapter for compactly assembling a socket adapter gas detection and alarm system.

According to the present invention, the gas detection and alarm system for monitoring carbon monoxide and other gases, comprises detection means for detecting a predetermined dose of gas; indication means for indicating the dose detection to the user detected by said detection means; microprocessor means for digitally operating said indication and detection means; power conversion means for supplying constant power to said detection and indication means; and housing means for housing said detection, indication, microprocessor and power conversion means.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only and, thus, are not limitative of the present invention, and wherein.

DETAILED DESCRIPTION OF THE PREFERRED EMBODIMENTS

Figure 1:
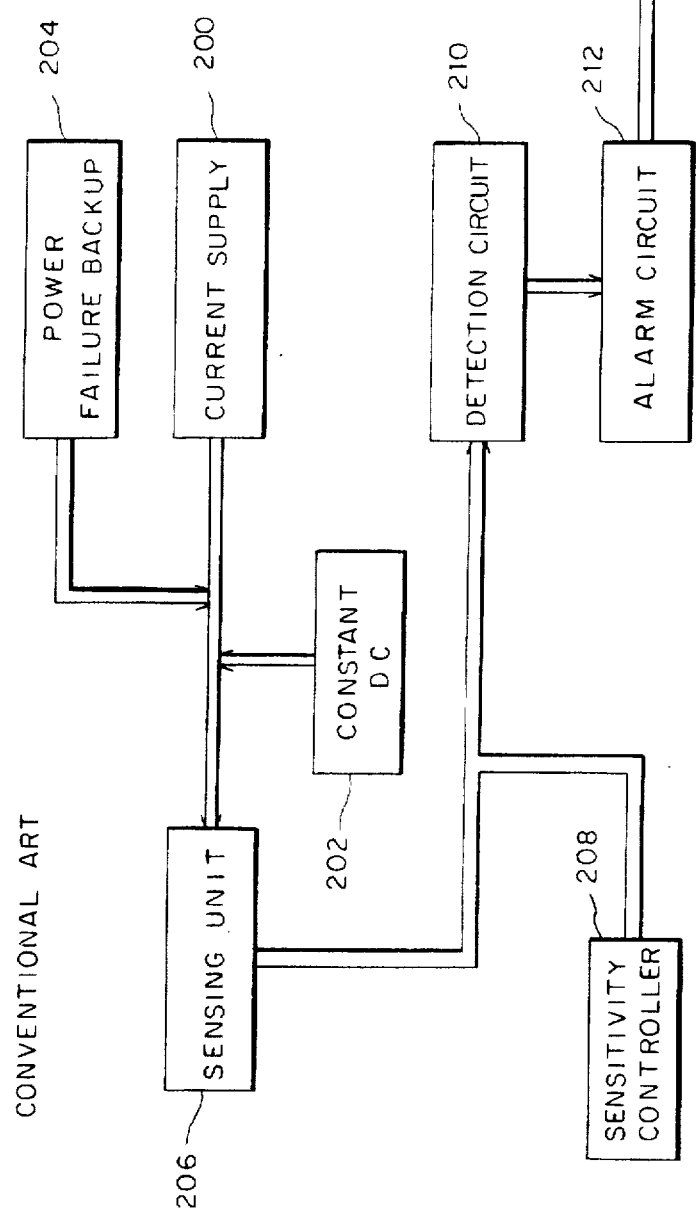
FIG. 1 is a block diagram of a conventional gas detection and alarm system.
Figure 2:
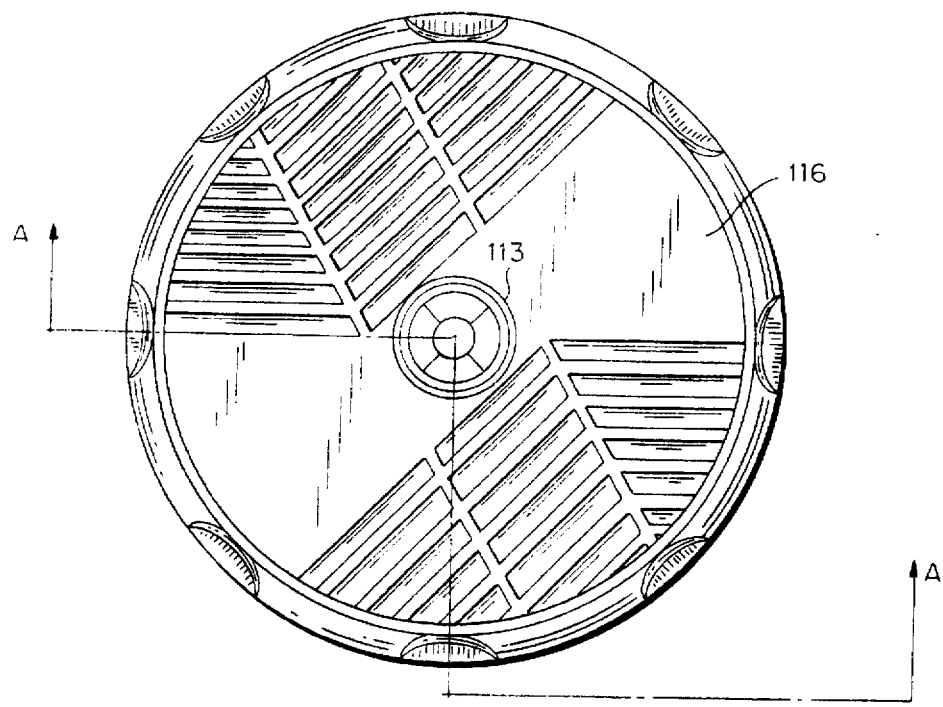
FIG. 2 is a top view of a gas detection/alarm device according to the present invention.
Figure 2A:
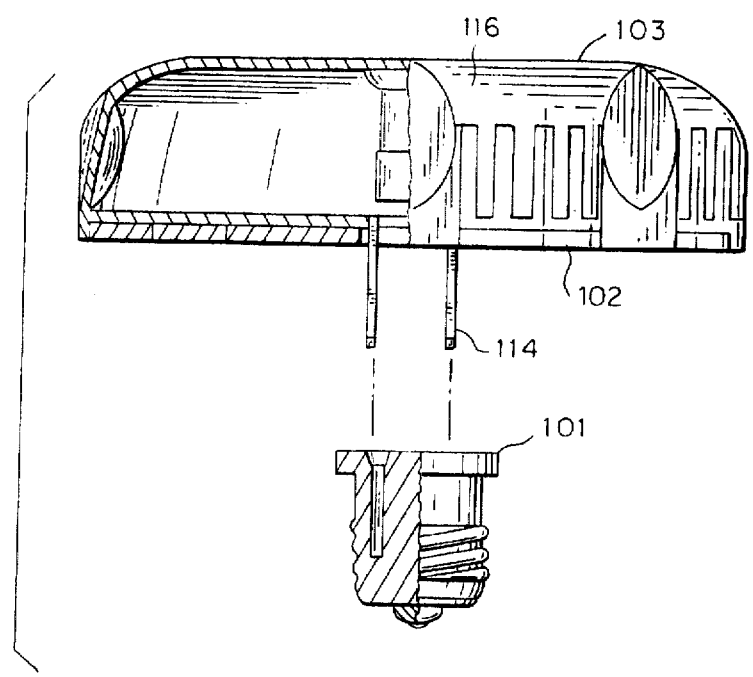
FIG. 2A is a sectional view of the gas detection/alarm device, taken on line A—A of FIG. 2.

Referring now in detail to the drawings for the purpose of illustrating the preferred embodiments of the present invention, the gas detection and alarm system for monitoring a predetermined level of gas such as carbon monoxide, as shown in FIGS. 2, 2A, 3 and 3A according to an embodiment of the present invention, comprises a gas detection/alarm device 116 having a round top cover 103 and a bottom plate 102 for housing a plurality of electronic circuits 104, 105, a light indicator 113, and an electric plug 114 for engaging a test and reset button, with a power source, such as, an electric outlet. The alarm device 116 can be easily engaged with a light bulb socket using a socket receiver 101. By engaging the electric plug 114 of the alarm device 116 with the receiver 101, the alarm device 116 can be screwed into any electric outlet.

The circuits 104 and 105, which are mounted on the bottom plate 102 of the gas alarm device 116, are a transformerless AC to DC power conversion circuit 104 and an analog gas detection/alarm circuit 105, respectively. The power conversion circuit 104 does not employ any transformers to provide AC to DC power conversion and, therefore, is an inexpensive and a compact way to provide a gas detection and alarm system for monitoring carbon monoxide. The power conversion circuit 104 includes resistors R8–R11; capacitors C5–C9; 33-volt, 10-watt zener diode D1; 3-amp, 1000-PIV silicon rectifier diode D2; small signal, silicon diodes D3, D4; and 8-amp, 400-PIV silicon-controlled rectifier SCR1 mounted on a heat sink. In the power conversion circuit 104, following resistance and capacitance values, for example, can be utilized.

| Resistor | Ω-ohms | Capacitor | Capacitance |
| --- | --- | --- | --- |
| R8  | 5     | C5 | 0.47 µF  |
| R9  | 330 K | C6 | 1.0 µF   |
| R10 | 100 K | C7 | 0.56 µF  |
| R11 | 100 K | C8 | 2,500 µF |

The detection/alarm circuit 105 includes 6 Ni-Cd cell battery B1; silicon diodes D1,D2; light emitting diode LED; silicon-controlled rectifier SCR2; SPST miniature switch S1; IC chip IC1 for maintaining constant DC power; gas sensor 118 for sensing a predetermined gas level which is harmful to humans; sensitivity setting resistor R4 for controlling the sensitivity of the gas sensor 118; and piezoelectric buzzer BUZZ for generating an alarm sound when the predetermined gas level for a gas, such as carbon monoxide, is detected. In the detection/alarm circuit 105, following resistance and capacitance values, for example, can be utilized.

| Resistor | Ω-ohms | Capacitor | Capacitance |
| --- | --- | --- | --- |
| R1 | 100  | C1 | 220 µF |
| R2 | 15   |    |        |
| R3 | 270  |    |        |
| R4 | 50 K |    |        |

Figure 4:
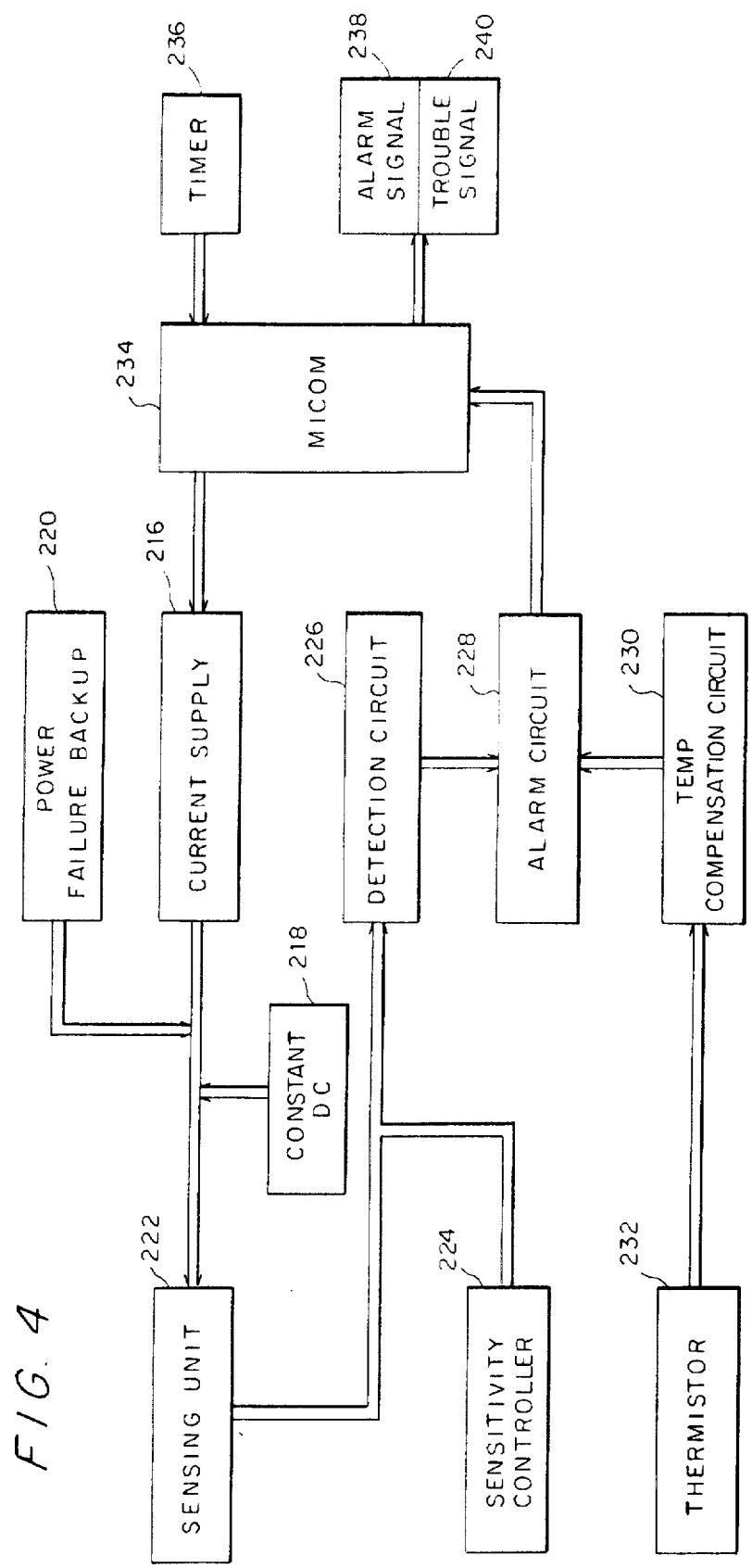
FIG. 4 is a block diagram of a gas detection and alarm system according to the present invention.

Referring to FIG. 4, there is illustrated a block diagram of a preferred embodiment of the gas detection and alarm system according to the present invention. The gas detection and alarm system of the present invention includes a current supply 216, a constant DC circuit 218 for supplying constant DC power to a sensing unit 222 which senses a predetermined gas level for a gas such as carbon monoxide, a power failure backup circuit 220 for providing alternative power in the event of a power failure, and a detection circuit 226 for determining whether or not the predetermined dose of carbon monoxide and other gasses exists in the atmosphere.

By employing a sensitivity controller 224 having, for example, a variable resistor, the sensitivity of the sensing unit 222 can be controlled by varying the resistance of the resistor. When the detection circuit 226 detects inappropriate, predetermined gas dose, an alarm circuit 228 generates audio alarm signal 238 to alert the user.

The gas alarm system as shown in FIG. 4 further includes a temperature compensating circuit 230 for sustaining a constant temperature for the alarm circuit 228, a thermistor 232 for the temperature compensation circuit 230, a microprocessor 234 for digitally controlling the present alarm system and generating visual trouble signal 240, and a timer 236 for the microprocessor 234. The microprocessor 234 controls generation of both the audio alarm signal 238 and the visual trouble signal 240 to activate visual and audible indicators. The activation of these indicators alerts the user that inappropriate dose of gas, such as carbon monoxide, is detected in the atmosphere.

Figure 5:
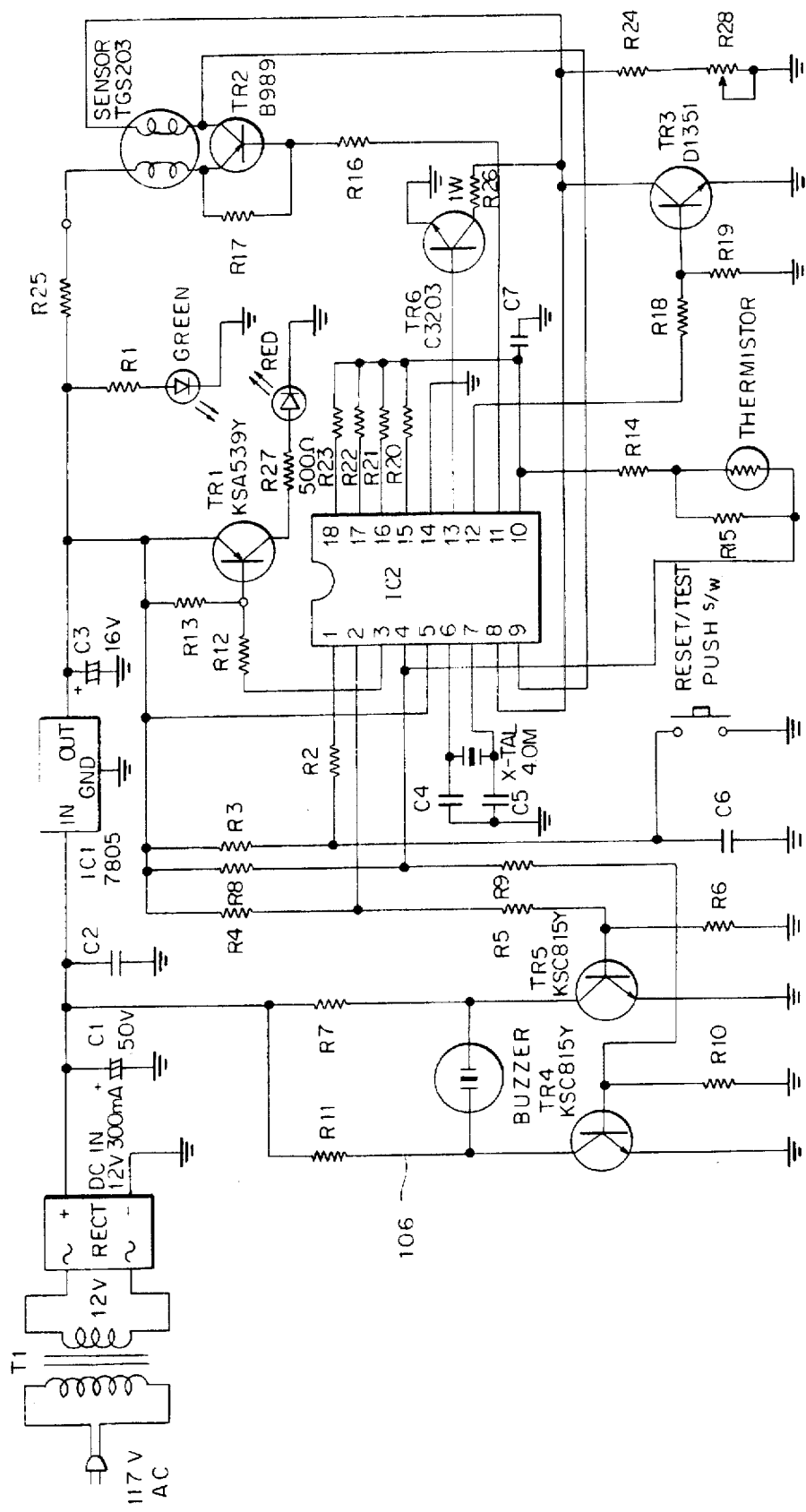
FIG. 5 is a schematic diagram of a gas detection/alarm circuit according to an embodiment of the present invention.

Referring to FIG. 5, a digital gas detection/alarm circuit 106 according to an embodiment of the present invention receives a constant DC voltage generated by a transformer T1 and a rectifier RECT from 117 VAC. This digital circuit 106 is a modification of the gas detection/alarm circuit 105 shown in FIG. 3 (described hereinabove) and incorporates a microprocessor IC2 therein. Therefore, the digital circuit 106 can be substituted for the detection/circuit 105 of FIG. 3.

As shown in FIG. 5, the gas detection/alarm circuit 106 includes resistors R1–R27; variable resistor R28 (=500K, for example) for controlling the sensitivity of a gas sensor TGS203 which senses a predetermined gas dose; capacitors C1–C7; IC chip IC1 for maintaining a constant DC voltage; green LED which is activated when the detection circuit is in a normal mode or in a reset mode; red LED which is activated when the detection circuit detects a harmful gas dose; silicon transistors TR1–TR6; a reset/test switch S/W for resetting the system after each gas dose detection indicated by the red light; 4.0 MHz ceramic resonator X-TAL; microprocessor IC2 for digitally operating the gas detection/alarm circuit 106; piezo-electric buzzer for generating audio alarm when a predetermined gas dose is detected; and 5K thermistor having variable resistance which changes with a temperature change. As mentioned above, the circuit 106 can be implemented into the gas alarm device 116 shown in FIG. 3 in lieu of the detection/alarm circuit 105, whereby the green light from the green LED is emitted through the indicator 113 to indicate that the present system is in normal operation, or otherwise, the red light from the red LED is emitted to alert the user that the predetermined gas dose is detected by the system. The reset switch S/W of the circuit 106 can be operatively connected to the indicator 113 so that the indicator 113 can be pushed in to activate the reset switch S/W for terminating the red light emission and, at the same time, for reactivating the green light emission. In the detection/alarm circuit 106, following resistance and capacitance values, for example, can be utilized.

| Resistor | Ω-ohms | Capacitor | Capacitance |
| --- | --- | --- | --- |
| R1, R15           | 4.7 K | C1 | 470 µF |
| R2, R4–R6, R8–R10 | 3.9 K | C2 | 0.1 µF |
| R3                | 10 K  | C3 | 47 µF  |
| R7, R11           | 500   | C4 | 20 pF  |
| R12, R13, R16–R19 | 1.0 K | C5 | 20 pF  |

-continued

| Resistor | Ω-ohms | Capacitor | Capacitance |
|---|---|---|---|
| R24 | | | |

| Resistor | Ω-ohms | Capacitor | Capacitance |
|---|---|---|---|
| R14 | 470 | C6 | 0.1 μF |
| R20 | 9.1 K | C7 | 0.10. F |
| R22 | 750 | | |
| R21, R23 | 270 | | |
| R25 | 3.0 | | |
| R26 | 20 | | |
| R27 | 500 | | |

Figure 6:
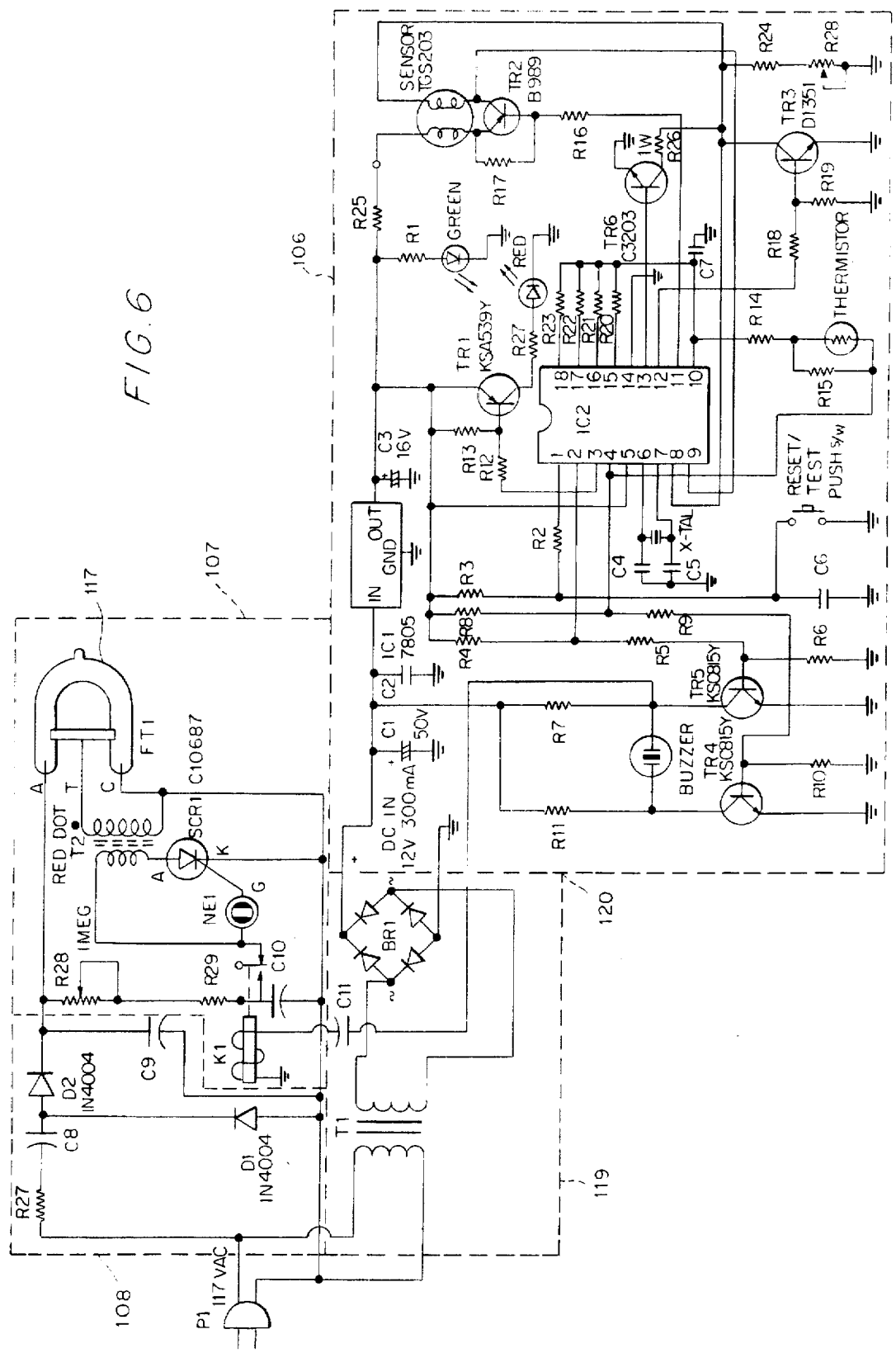
FIG. 6 is a schematic diagram of a gas detection/alarm circuit having a strobe light trigger circuit according to another embodiment of the present invention.

Referring to FIG. 6, there is shown a schematic diagram of a preferred embodiment of the gas detection and alarm system according the present invention comprising a digital gas detection/alarm circuit 106 having a microprocessor and a buzzer (see FIG. 5 for a detailed description); AC to DC power conversion circuit 119 having a transformer T1, a rectifier BR1 and a capacitor C11 (=1.0 MF, for example) for supplying constant power to the digital circuit 106; a strobe light trigger circuit 107; a voltage doubler circuit 108 for supplying a constant voltage to the trigger circuit 107; and a housing unit 120 for housing the detection/alarm circuit 106, power conversion circuit 119, trigger circuit 107 and voltage double circuit 108.

As shown in FIG. 6, this embodiment includes a variable strobe light tube 117 in addition to the green and red LEDs, to more actively alert the user of a harmful gas dose detection in addition to the alarm sound from the buzzer. The use of a strobe light source is highly advantageous because high-intensity white light having short durations can be emitted. Furthermore, the speed or flash rate of the emission is variable from one or two light pulses per minute to 12 or more pulses per second. Moreover, the strobe light tube 117 consumes less power in comparison with other well known light sources.

The operation of the strobe light tube 117 as a visual indicator for the gas alarm system of the present invention is as follows.

The strobe light tube 117 filled with inert gas, such as xenon, includes two ends being the anode (+) and the cathode (−). The strobe light tube 117 also includes a third electrode called the trigger which is strapped around the outside of the light tube 117 in the vicinity of the two electrodes. The light tube 117 is activated using two voltages, 320 volts DC or more applied between the cathode and the anode and pulses of approximately 4,000 volts applied to the trigger electrode.

In order to activate the light tube 117, it is necessary to apply both 320 volts DC and a pulse of 4,000 volts to the tube. When the trigger electrode receives the pulse of 4,000 volts, some of the xenon gas particles in the light tube 117 are ionized due to the high voltage gradient developed in the vicinity the anode and cathode having 320 volts DC applied therebetween. Then the free electrons flow through the xenon inert gas to the positive anode of the light tube 117 at a very high speed. Impacts from the interaction between the inert gas atoms and the fast-moving free electrons create more free electrons in an avalanche fashion, until there exists enough free electrons to rapidly discharge a capacitor in an instant (i.e., a fraction of a millisecond). This results in a flash of bright light as this sudden, large current passes through the light tube 117.

Accordingly, two circuits, a voltage doubler circuit 108 and a trigger circuit 107, are utilized to activate the strobe light tube 117. The voltage doubler circuit 108 charges a capacitor for placing 320 volts DC between the cathode and the anode of the light tube 117. The trigger circuit 107 generates pulses of approximately 4,000 volts for firing the light tube.

The voltage doubler circuit 108 operates by sending two equal voltages in series which results in a doubling of the applied voltage. During a one-half cycle of the applied voltage of 117 volts AC, capacitor C8 is charged to serve as a "battery" for the next half cycle of the AC line voltage. During the next half cycle of the AC line voltage, a current flows through capacitor C9 and establishes a voltage of 320 volts DC across the capacitor C9. The voltage across the capacitor C9 is doubled because the doubler circuit 108 adds 160 volts DC across the capacitor C8 and 160 volts DC across the AC line voltage. The line voltage is now in series with the capacitor C8 and the capacitor C9 is fully charged to place 320 volts DC across the strobe light tube 117.

In reality, the capacitors C8 and C9 are not directly charged up to the peak voltage in one cycle of the AC line voltage. Instead, it takes several cycles to charge these capacitors but, since the fastest flash rate has about 5 full-cycles of the AC line voltage, the maximum DC voltage can be always achieved by the voltage doubler circuit before the light tube is fired. Even after each flash, the voltages across the capacitors C8 and C9 never drop to zero.

The strobe light trigger circuit 107 provides pulses of about 4,000 volts necessary to trigger or flash the light tube 117. The trigger circuit 107 includes a voltage set-up transformer T2 to deliver 4,000 volts across its secondary coil as the current flows in its primary coil. A silicon controlled rectifier SCR1 controls the current flow in the primary coil of the transformer T2. That is, when the rectifier SCR1 conducts, the current flows suddenly in the primary coil of the transformer T2 and a pulse of 4,000 volts AC appears across the secondary coil of the transformer T2.

As shown in FIG. 6, in order for the silicon control rectifier SCR1 to conduct, two elements are required:

a negative and a positive voltage applied to the cathode and the anode of the light tube 117, respectively, and a positive voltage on the gate of the rectifier SCR1.

The positive voltage on the gate of the rectifier SCR1 is provided by the components R28, R29, C10, and NE1. When 320 volts DC from the voltage doubler circuit 108 is applied across the variable resistor R28, resistor R29 and capacitor C10, the circuit begins to charge. The time it takes for the capacitor C10 to charge up to a predetermined level (much less than 320 volts) is determined by the total resistance of the resistors R28 and R29 and the size of the capacitor C10. It should be noted that the greater the total resistance and the larger the capacitor C10 is, the longer it takes for the capacitor C10 to charge. Accordingly, the charging time of the capacitor C10 can be controlled by varying the resistance of R28.

As the capacitor C10 is charged up to a high positive voltage (320 volts DC), the same voltage appears on the anode of the silicon controlled rectifier SCR1 via the primary coil of the transformer T2. As the negative return of the same voltage appears on the cathode of the rectifier SCR1, a positive voltage on the gate of the rectifier SCR1, which is provided by neon bulb NE1, shorts out the circuit. That is, when the voltage across the capacitor C10 reaches the firing voltage of the neon bulb NE1 which is around 65 to 70 volts, it causes the neon bulb NE1 to conduct and place a positive voltage on the gate of the rectifier SCR1. Due to this positive voltage, the rectifier SCR1 is short-circuited and the capacitor C10 is discharged through the rectifier SCR1 and the primary coil of the transformer T2. Then the high positive voltage of 4,000 volts developed across the secondary coil of the transformer T2 fires the flash tube 117 causing a bright flash. The above process is repeated and, thus, the flashes of the strobe light tube 117 are generated by the voltage doubler circuit 108 and the trigger circuit 107.

As shown in FIG. 6, the voltage doubler circuit 108 and the trigger circuit 107 further include rectifier diodes D1,D2, resistor R29, capacitors C8,C9 and a micro-mini PC relay K1. In the voltage doubler circuit 108 and the trigger circuit 107, following resistance and capacitance values, for example, can be utilized.

| Resistor | Ω-ohms | Capacitor | Capacitance |
| --- | --- | --- | --- |
| R27 | 1.0 K | C8 | 4.7 µF |
| R28 | 1.0 M | C9 | 22 µF |
| R29 | 47 K | C10 | 0.47 µF |
|  |  | C11 | 1.0 MF |

Figure 7:
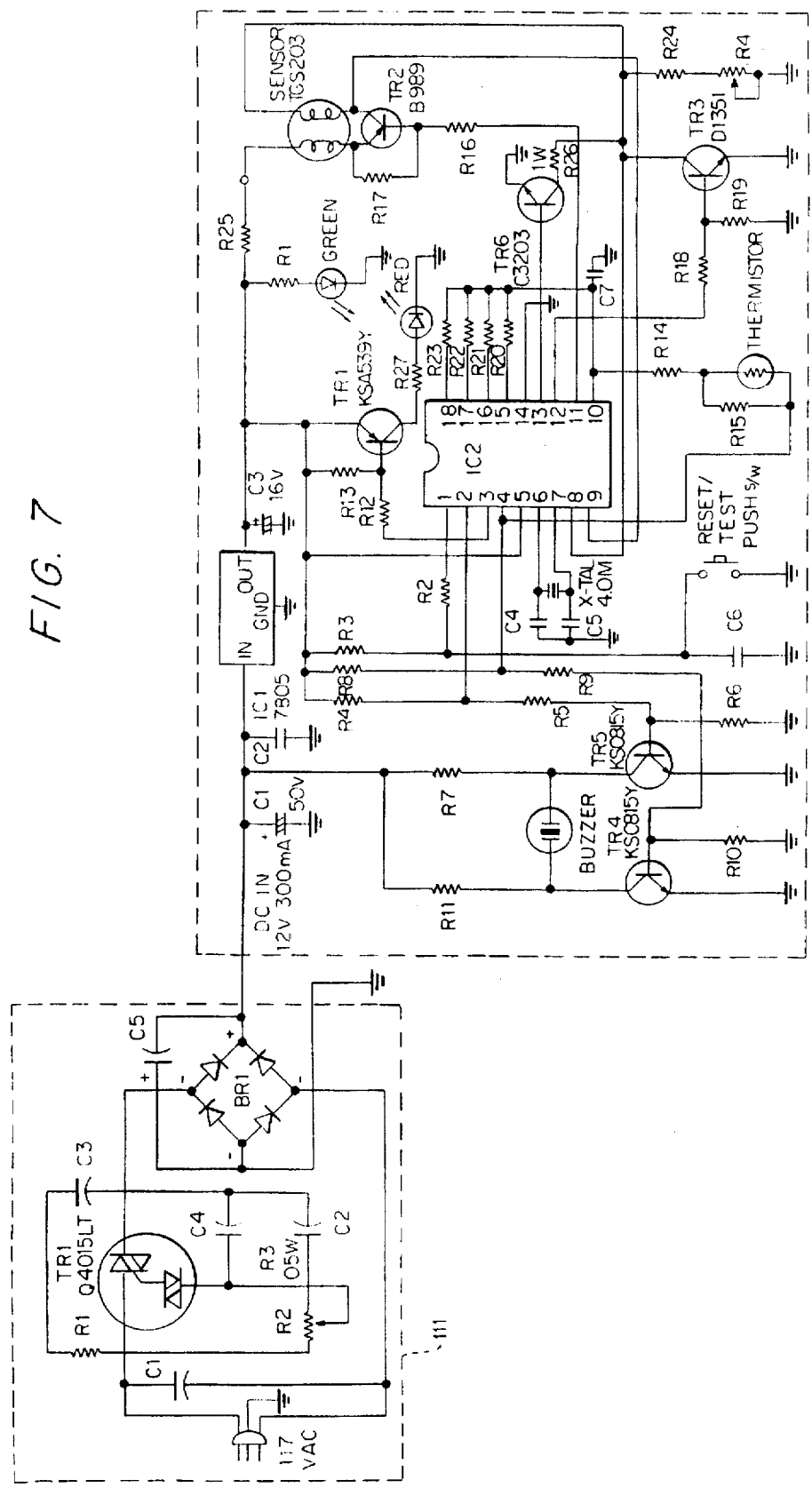
FIG. 7 is a schematic diagram of a gas detection/alarm circuit having a transformerless power supply according to another embodiment of the present invention.

Referring to FIG. 7 according to another embodiment of the present invention, the digital gas detection alarm circuit 106 (see FIG. 5 for a detailed description) is supplied with a constant DC voltage using AC to DC power conversion circuit 111. The circuit 111 includes AC source (117 VAC), resistors R1, R3, capacitors C1–C5, variable resistor R2, semiconductor triacs TR1, and a bridge rectifier BR1. In the power conversion circuit 111, following resistance and capacitance values, for example, can be utilized.

| Resistor | Ω-ohms | Capacitor | Capacitance |
| --- | --- | --- | --- |
| R1 | 100 | C1, C2, C4 | 0.1 µF |
| R2 | 100 K | C3 | 0.22 µF |
| R3 | 15 K | C5 | 1000 µF |

The power conversion circuit 111 generates smooth 0–10 amp DC output with minimal filtering at DC voltages as low as 10–15 volts. This power conversion circuit 111 utilizes a triac to build a low-cost, transformerless, variable power supply which is a cost-effective alternative for a number of applications that require minimal filtering. The circuit 111 includes no transformers and can be compactly mounted on the bottom plate 102 of the gas device 116 shown in FIG. 3A.

Figure 8:
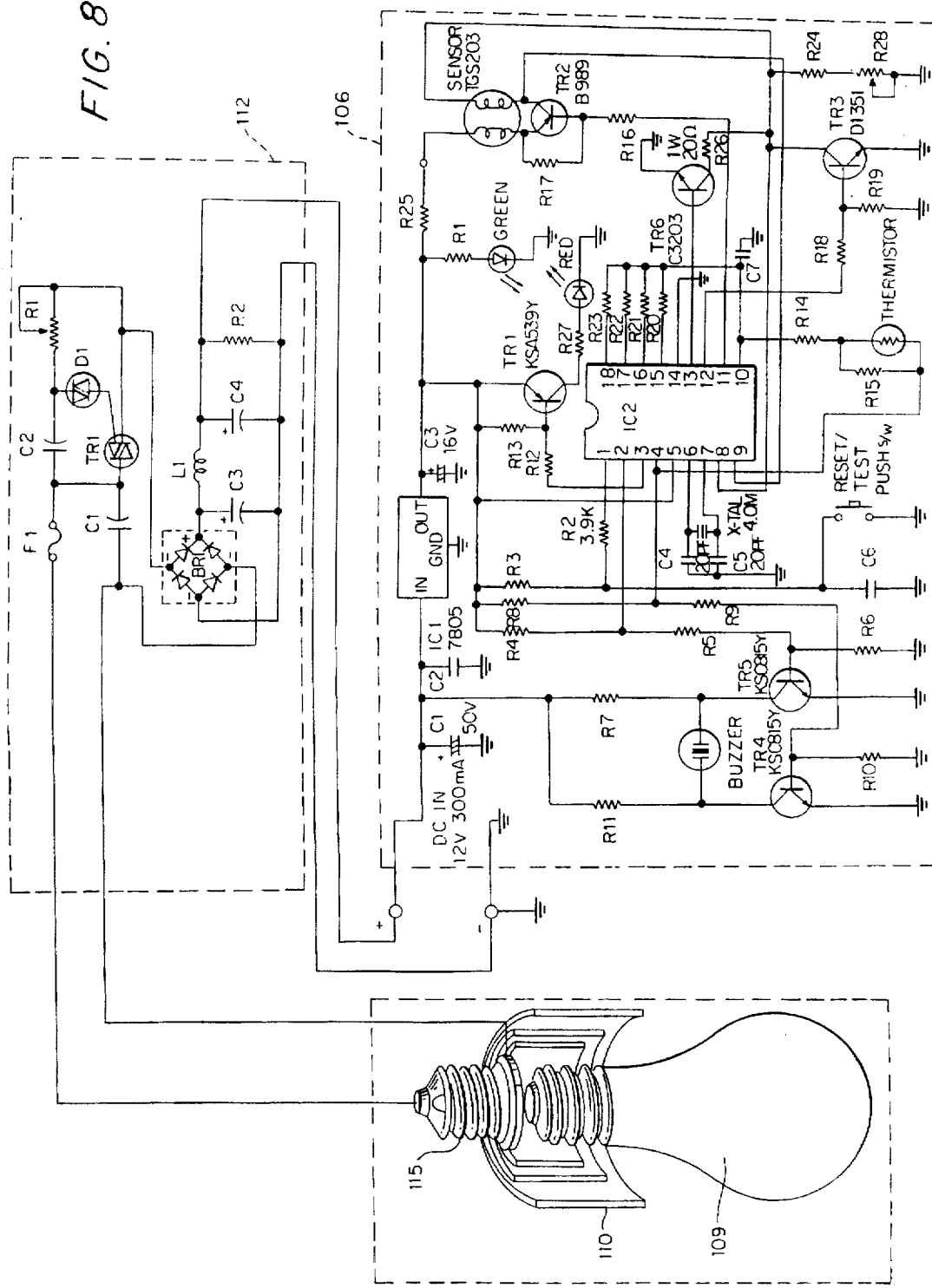
FIG. 8 is a schematic diagram of a gas detection and alarm system according to another embodiment of the present invention.

Referring to FIG. 8 according to another embodiment of the present invention, the digital gas detection and alarm circuit 106 (see FIG. 5 for a detailed description) is connected to another transformerless AC to DC power conversion circuit 112. The conversion circuit 112 includes diac D1, traic TR1, resistors R1,R2, capacitors C1–C4, fuse F1 for 5–10 amp, core inductance L1, and a bridge rectifier BR1. Following resistance and capacitance values, for example, can be utilized.

| Resistor | Ω-ohms | Capacitor | Capacitance |
| --- | --- | --- | --- |
| R1 | 250 K | C1 | 0.05 µF |
| R2 | 100 K | C2 | 0.1 µF |
|  |  | C3, C4 | 47 µF |

As shown in FIG. 8, the conversion circuit 112 receives AC voltage via a light bulb socket 115 whose use with a light bulb 109 is well known to the user. Both the transformerless conversion circuit 112 and the digital detection/alarm circuit 106 are integrated into a socket adapter 110 of the light bulb 109 for insertion into the light bulb socket 115. This feature of the embodiment allows the present gas detection/alarm system to be incorporated into a light bulb system having a socket adapter and a socket, and to conveniently install a gas detection/alarm system into the light bulb system.

Figures 3, 3A:
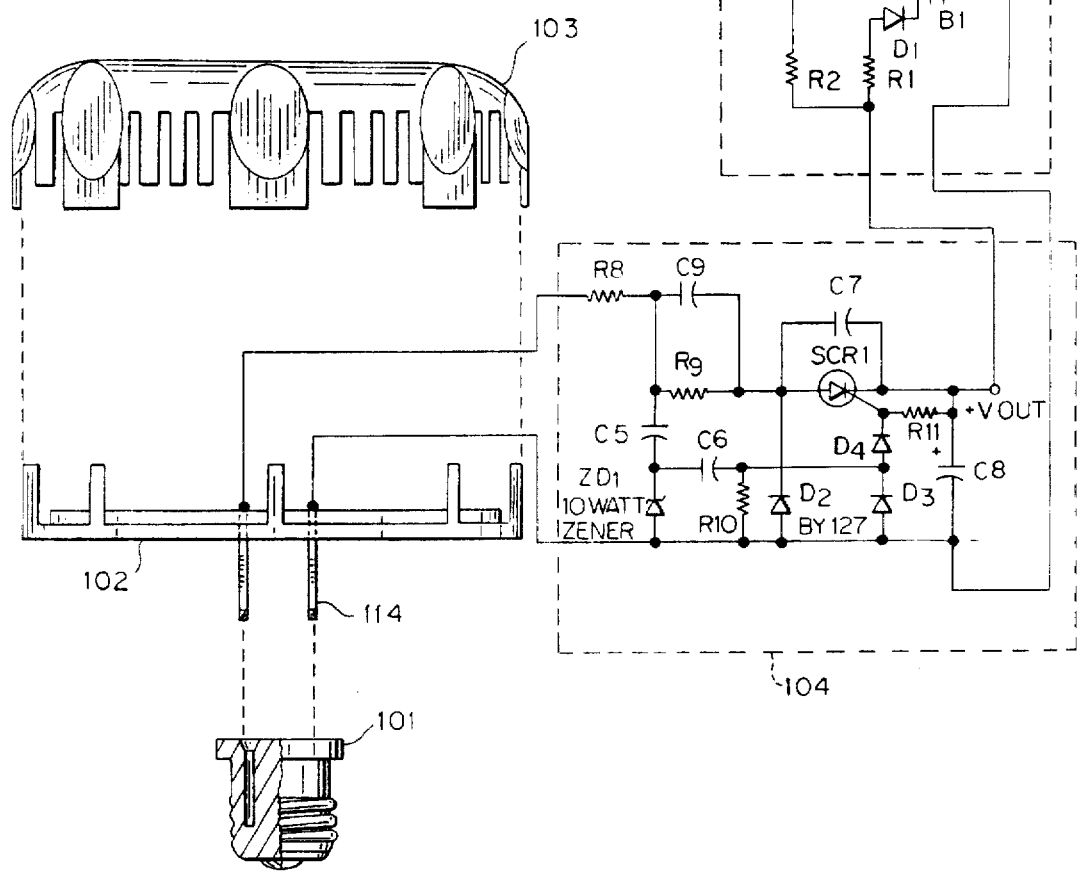
FIGS. 3 and 3A are top and side views of a gas detection and alarm system according to an embodiment of the present invention.

Also, since the power conversion circuit 112 includes no transformers, it can be compactly mounted on the bottom plate 102 of the gas detection/alarm device 116 shown in FIG. 3. Furthermore, the circuit 112 can be substituted with any one of the transformerless AC to DC power conversion circuits 104, 111 described hereinabove.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A gas detection and alarm system for monitoring carbon monoxide, comprising:

detection means for detecting a predetermined dose of carbon monoxide, the detection means including a semiconductor-type carbon monoxide sensor having a plurality of connections connected to at least three terminals of a microprocessor through a plurality of transistors;

indication means for indicating the dose detected by the detection means to the user, said indication means including a temperature compensating circuit for maintaining a constant temperature thereof;

microprocessor means including the microprocessor for digitally controlling said indication and detection means;

power conversion means for supplying constant power to said detection and indication means;

housing means for housing said detection, indication, microprocessor and power conversion means, wherein said housing means has a circular configuration and includes an electric plug disposed on a bottom surface of said housing means, and said indication means includes a buzzer for generating an audio sound and a first transistor directly connected to said buzzer;

wherein said housing means further includes:

a top cover having a light emitting portion, and a bottom plate having said electric plug and a surface for mounting thereon said indication, power conversion, microprocessor, and detection means in a substantially coplanar manner, said top cover and bottom plate engaging each other to form a housing unit;

wherein said light emitting portion includes a movable switch for resetting the system after activation of said indication means to indicate said dose detection; and wherein said power conversion means includes a power conversion circuit having no transformers, said conversion circuit receiving AC power and generating constant DC power from said AC power.

2. The system of claim 1, wherein said indication means includes at least one light source which emits light, said buzzer and said at least one light source audibly and visually indicating said detection of predetermined dose of gas, respectively.

3. The system of claim 2, wherein said at least one light source includes a plurality of light emitting diodes for emitting different color of light, said different color of light including a green light and a red light being alternatively emitted through said housing means based on said dose detection by said detection means.

4. The system of claim 3, wherein said green light is emitted when the system is in normal operation mode or in a reset mode, and the red light is emitted when said predetermined dose of gas is detected, said emission of red light and said audio sound from the buzzer being terminated when the movable switch is activated.

5. A gas detection and alarm system for monitoring carbon monoxide, comprising:

- detection means for detecting a predetermined dose of carbon monoxide, the detection means including a semiconductor-type carbon monoxide sensor having a plurality of connections connected to at least three terminals of a microprocessor through a plurality of transistors;
- indication means for indicating the dose detected by the detection means to the user, said indication means including a temperature compensating circuit for maintaining a constant temperature thereof;
- microprocessor means including the microprocessor for digitally controlling said indication and detection means;
- power conversion means for supplying constant power to said detection and indication means;
- housing means for housing said detection, indication, microprocessor and power conversion means;
- strobe light emitting means for emitting a strobe light when said predetermined dose of gas is detected;
- trigger means for triggering said strobe light; and
- voltage doubler means for supplying constant voltage to said trigger means and said strobe light emitting means, wherein said housing means includes:

- a top cover having a light emitting portion, and
- a bottom plate having an electric plug and a surface for mounting thereon said indication power conversion, microprocessor, and detection means in a substantially coplanar manner, said top cover and bottom plate engaging each other to form a housing unit.

6. The system of claim 5, wherein said strobe light emitting means includes a strobe light tube having a plurality of electrodes, said trigger means including a trigger circuit for applying a plurality of pulses of volts to one of said plurality of electrodes.

7. The system of claim 6, wherein said voltage doubler means includes a voltage doubler circuit for doubling voltage applied to said doubler circuit and generating constant doubled voltage, said doubled voltage being applied to both said trigger circuit for generating said plurality of pulses of volts and to said light tube.

8. The system of claim 7, wherein said strobe light are emitted when both said constant doubled voltage and said plurality of pulses of volts are applied to said light tube.

* * * * *